(12) United States Patent
Gelboin et al.

(10) Patent No.: US 6,335,428 B1
(45) Date of Patent: Jan. 1, 2002

(54) AGENTS THAT BIND TO AND INHIBIT HUMAN CYTOCHROME P450 1A2

(75) Inventors: Harry V. Gelboin, Chevy Chase; Frank J. Gonzalez, Bethesda, both of MD (US); Tian J. Yang, Hockenssin, DE (US)

(73) Assignee: The United States of America as represented by the Department of Health and Human Services, Rockville, MD (US)

(*) Notice: Subject to any disclaimer, the term of this patent is extended or adjusted under 35 U.S.C. 154(b) by 0 days.

(21) Appl. No.: 09/289,766

(22) Filed: Apr. 8, 1999

Related U.S. Application Data
(60) Provisional application No. 60/093,913, filed on Jul. 23, 1998.

(51) Int. Cl.$^7$ .................... G01N 33/573; G01N 33/577; C07K 16/00; C12P 21/08

(52) U.S. Cl. ........................ 530/388.1; 435/4; 435/5; 435/6; 435/7; 435/7.21; 435/25; 435/40.5; 435/40.51; 435/40.52; 435/69.6; 435/252.1; 435/968; 435/805; 435/7.1; 436/69; 436/166; 436/169; 436/170; 436/501; 436/503; 530/387.1; 530/387.3; 530/387.7; 530/388.15; 530/388.26; 530/387.9; 530/388.85; 424/141.1

(58) Field of Search ................. 435/4, 5, 6, 7, 435/7.1, 7.21, 69.6, 968, 805, 252.1, 25, 40.5, 40.51, 40.52; 436/69, 166, 169, 170, 501, 53; 530/387.1, 387.3, 387.9, 388.1, 388.15, 388.85, 388.26, 387.7

(56) References Cited

U.S. PATENT DOCUMENTS
5,939,530 A  8/1999  Gelboin et al. ........... 530/387.1

FOREIGN PATENT DOCUMENTS
| WO | WO 91/17271 | * 11/1991 | ........... C12Q/1/70 |
| WO | WO 92/01047 | * 1/1992 | ........... C12N/15/00 |

OTHER PUBLICATIONS

Adams et al., "Specific inhibition of human CYP1A2 using a targeted antibody.", Biochemical Pharmacology, vol. 54, pp. 189–197, 1997.*
Buters, J. T. M. et al., "cDNA–directed expression of human cytochrome P450 CYP3A4 using baculovirus," *Drug Metabolism and Disposition*, 22:688–692, (1994).
Buchert, et al., "Clinical Implications of Variable Antiarrhythmic Drug Metabolism," *Pharmacogenitics*, 2:2–11, (1992).
Dahl, et al., "Genetically Variable Metabolism of Antidepressants and Neuroleptic Drugs in Man," *Pharmacogenetics*, 3:61–70 (1993).
Gelboin H. V., "Cytochrome P450 and monoclonal antibodies," *Pharmacol Rev*, 45(4):413–453, (1993).
Gelboin, H. V. et al., "Inhibitory and noninhibitory monoclonal antibodies to human cytochrome P450 2E1," *Chem Res Toxicol*, 9(6):1023–1030, (1996).
Gelboin, H. V. et al., "Inhibitory and non–inhibitory monoclonal antibodies to human cytochrome P450 3A3/4," *Biochem Pharmacol*, 50(11):1841–1850, (1995).
Gelboin, H. V. et al., "A monoclonal antibody inhibitory to human P450 2D6: a paradigm for use in combinatorial determination of individual P450 role in specific drug tissue metabolism," *Pharmacogenetics*, 7:469–477, (1977).
Gonzalez, F. J. et al., "Characterization of the common Genetic Defect in Humans Deficient in Debrisoquine Metabolism," *Nature*, 331(6155):442–446, (Feb. 4, 1988).
Gonzalez, F. J. et al., "Role of Human Cytochrome P–450s in Risk Assessment and Susceptibility to Environmentally Based Disease," *J. Toxicol. and Environmental Health*, 40:289–308, (1993).
Gonzalez, F. J. et al., "Expression of mammalian cytochrome P450 using baculovirus," *Methods Enzymol*, 206:93–9, (1991b).
Gonzalez, F. J. et al., "cDNA–expressed human cytochrome P450s: a new age of molecular toxicology and human risk assessment," *Mutat. Res.*, 247:113–127, (1991a).
Guengerich, F. P., "Human cytochrome P450 enzymes," P. R. Ortiz de Montellano, Ed. *Cytochrome P450: structure, mechanism, and biochemistry*, New York: Plenum Press, pp. 473–535, (1995).
Krausz, K. W. et al., "Inhibitory monoclonal antibodies to human cytochrome P450 2D6," *Biochem Pharmacol*, 54:15–17, (1997).
Mineshita, S. et al., "Determination of phenacetin and its major metabolites in human plasma and urine by high–performance liquid chromatography," *J Chromatogr*, 380:407–13, (1986).
Nelson, D. R. et al., "P450 superfamily: update on new sequences, gene mapping, accession numbers and nomenclature," *Pharmacogenetics*, 6:1–42, (1996).
Park, S. S. et al., "Monoclonal antibodies that inhibit enzyme activity of 3–methylcholanthrene–induced cytochrome P–450," *Cancer Res*, 42:1798–1808, (1982).
Park, S. S. et al., "Monoclonal antibodies to rat liver cytochrome P–450 2c/RLM5 that regiospecifically inhibit steroid metabolism," *Biochem Pharmacol*, 38:3067–74, (1989).

(List continued on next page.)

Primary Examiner—Long V. Le
Assistant Examiner—Lisa V. Cook
(74) Attorney, Agent, or Firm—Townsend & Townsend & Crew LLP

(57) ABSTRACT

The invention provides monoclonal antibodies and other binding agents to human cytochrome P450 1A2 having advantageous properties, including capacity substantially to inhibit enzyme activity of human cytochrome P450 1A2 and lack of specific binding to other human cytochromes P450. The binding agents of the invention are useful inter alia in methods for screening drugs for metabolism by cytochrome P450 1A2, and in methods of measuring p450 1A2 levels in individuals relative to p450 1A2 levels in a control population.

8 Claims, 4 Drawing Sheets

OTHER PUBLICATIONS

Rendic, S. et al., "Human cytochrome P450 enzymes: a status report summarizing their reactions, substrates, inducers, and inhibitors," *Drug Metab. Rev,* 29:413–580, (1997).

Tassaneeyakul, W. et al., "Specificity of substrate and inhibitor probes for human cytochromes P450 1A1 and 1A2," *J Pharmacol Exp Ther,* 265:401–7, (1993).

Vermeulen, N. P. E., *Role of metablism in chemical toxicity. In: C. Ioannides, Ed. Cytochromes P450: metabolic and toxicological aspects,* CRC Press, pp. 29–53, (1996).

von Moltke, L. L. et al., "Phenacetin O–deethylation by human liver microsomes in vitro: inhibition by chemical probes, SSRI antidepressants, nefazodone and venlafaxine," *Psychopharmacology,* (Berl) 128:398–407, (1996).

Yamazaki, H. et al., "7–Ethoxycoumarin O–deethylation catalyzed by cytochromes P450 1A2 and 2E1 in human liver microsomes," *Biochem Pharmacol,* 51:313–319, (1996).

Yang, T. J. et al., "An inhibitory monoclonal antibody to human cytochrome P450 2B6," *Biochem. Phamacol,* 55(10):1633–40, (1998).

Yang, T. J. et al., "Role of cDNA–expressed human cytochromes P450 in the metabolism of diazepam," *Biochemical Pharmacology,* 55(6):889–96, (1998).

Pelkonen, O. et al., "Coumarin 7–hydroxylase: characteristics and regulation in mouse and man," *J Irish Coll Phys Surg,* 22:24–28, (1993).

* cited by examiner

AGENTS THAT BIND TO AND INHIBIT HUMAN CYTOCHROME P450 1A2

CROSS-REFERENCES TO RELATED APPLICATIONS

This application claims the benefit of U.S. Provisional Application No. 60/093,913 filed Jul. 23, 1998, the disclosure of which is incorporated by reference.

TECHNICAL FIELD

The present invention resides in the technical fields of immunology and enzymology.

BACKGROUND OF THE INVENTION

The cytochrome P450 family of enzymes is primarily responsible for the metabolism of xenobiotics such as drugs, carcinogens and environmental chemicals, as well as several classes of endobiotics such as steroids and prostaglandins. Members of the cytochrome P450 family are present in varying levels and their expression and activities are controlled by variables such as chemical environment, sex, developmental stage, nutrition and age.

More than 200 cytochrome P450 genes have been identified. There are multiple forms of these P450 and each of the individual forms exhibit degrees of specificity towards individual chemicals in the above classes of compounds. In some cases, a substrate, whether it be drug or carcinogen, is metabolized by more then one of the cytochromes P450.

Human cytochrome P450 1A2 constitutes about 13% of total P450 in human liver and is the second most abundant P450 following human cytochrome P450 3A4 (Vermeulen, 1996). P450 1A2 catalyzes the metabolism of a large variety of drugs and carcinogens (Rendic et al., 1997). Drugs metabolized by human P450 1A2 include phenacetin, R-warfarin, clomipramine, imipramine, theophyline, theobromine, paraxanthine, caffeine, chlorzoxazone, 7-methoxyresorufin, and 7-ethoxycoumarin. P450 1A2 is also has a major role in activating mutagens and carcinogens. For example, 1A2 metabolically activates the food pyrolysis products IQ and MeIQx to active mutagens (Edwards et al., 1994; Rendic et al., 1997).

Genetic polymorphisms of cytochromes P450 result in phenotypically-distinct subpopulations that differ in their ability to perform biotransformations of particular drugs and other chemical compounds. These phenotypic distinctions have important implications for selection of drugs. For example, a drug that is safe when administered to most humans may cause toxic side-effects in an individual suffering from a defect in an enzyme required for detoxification of the drug. Alternatively, a drug that is effective in most humans may be ineffective in a particular subpopulation because of lack of a enzyme required for conversion of the drug to a metabolically active form. Further, individuals lacking a biotransformation enzyme are often susceptible to cancers from environmental chemicals due to inability to detoxify the chemicals. Eichelbaum et al., *Toxicology Letters* 64/65, 155–122 (1992). Accordingly, it is important to identify individuals who are deficient in a particular P450 enzyme, so that drugs known or suspected of being metabolized by the enzyme are not used, or used only with special precautions (e.g., reduced dosage, close monitoring) in such individuals. Identification of such individuals may indicate that such individuals be monitored for the onset of cancers.

Existing methods of identifying deficiencies in patients are not entirely satisfactory. Patient metabolic profiles are often assessed with a bioassay after a probe drug administration. Individuals with below normal cytochrome P450 activity exhibit physiologic accumulation of unmodified drug and have a high metabolic ratio of probe drug to metabolite. This bioassay has a number of limitations: lack of patient cooperation, adverse reactions to probe drugs, and inaccuracy due to coadministration of other pharmacological agents or disease effects. See, e.g., Gonzalez et al., *Clin. Pharmacokin.* 26, 59–70 (1994). Genetic assays by RFLP (restriction fragment length polymorphism), ASO PCR (allele specific oligonucleotide hybridization to PCR products or PCR using mutant/wild-type specific oligo primers), SSCP (single stranded conformation polymorphism) and TGGE/DGGE (temperature or denaturing gradient gel electrophoresis), MDE (mutation detection electrophoresis) are time-consuming, technically demanding and limited in the number of gene mutation sites that can be tested at one time.

A complication in patient drug choice is that most drugs have not been characterized for their metabolism by P450 1A2 and other cytochromes P450. Without knowing which cytochrome(s) p450 is/are responsible for metabolizing an individual drug, an assessment cannot be made for the adequacy of a patient's P450 profile. For such drugs, there is a risk of adverse effects if the drugs are administered to deficient metabolizers.

Monoclonal antibodies that specifically bind to 1A2 and inhibit its activity, if available, could be used to screen drugs for their metabolism by 1A2 and/or identify 1A2 deficient metabolizers by simple bioassays, thereby overcoming the problems in prior complicated methods discussed above. However, such monoclonal antibodies represent, at best, a small subset of the total repertoire of antibodies to human cytochrome P450 1A2, and have not hitherto been isolated. Although in polyclonal sera, many classes of antibody may contribute to inhibition of enzyme activity of P450 1A2 as a result of multiple antibodies in sera binding to the same molecule of enzyme, only a small percentage of these, if any, can inhibit as a monoclonal. A monoclonal antibody can inhibit only by binding in such a manner that it alone block or otherwise perturb the active site of an enzyme. The existence and representation of monoclonal antibodies with inhibitory properties thus depend on many unpredictable factors. Among them are the size of the active site in an enzyme, whether the active site is immunogenic, and whether there are any sites distal to the active site that can exert inhibition due to stearic effects of antibody binding. The only means of obtaining antibodies with inhibitory properties is to screen large numbers of hybridoma until one either isolates the desired antibody or abandons the task through failure.

Notwithstanding these difficulties, the present invention provides inter alia monoclonal antibodies that specifically bind to human cytochrome P450 1A2 and inhibit its activity.

SUMMARY OF THE INVENTION

The invention provides isolated binding agents that compete with a monoclonal antibody selected from the group consisting of MAb 26-7-5, MAb 951-5-1, and MAb 1812-4-8 for specific binding to human cytochrome p450 1A2, and that specifically inhibit 1A2-catalyzed metabolism of phenacetin by at least 50%. Preferred binding agents are monoclonal antibodies. Some binding agents lacks specific binding to at least one cytochrome P450 selected from the group consisting of human cytochromes P450 1A1, 2A6, 2B6, 2C8, 2C9, 2C18, 2C19, 2D6, 2E1, 3A4, and 3A5.

Some binding agents lack specific binding to each of human cytochromes P450 1A1, 2A6, 2B6, 2C8, 2C9, 2C18, 2C19, 2D6, 2E1, 3A4, and 3A5. Preferred binding agents are able specifically to inhibit the enzyme activity of human cytochrome p450 1A2 by at least 80%. Some binding agents are binding fragments, such as Fab fragments.

MAb 26-7-5, MAb 951-5-1, and MAb 1812-4-8 are exemplified monoclonal antibodies. Some other monoclonal antibodies are analogs of these monoclonal antibodies comprising a light chain variable domain having at least 80% sequence identity with the light chain variable domain of a monoclonal antibody selected from the group consisting of MAb 26-7-5, MAb 951-5-1, and MAb 1812-4-8, wherein the percentage sequence identity is determined by aligning amino acids in the light chain variable domains by the Kabat numbering convention and a heavy chain variable domain having at least 80% sequence identity with the heavy chain variable domain of a monoclonal antibody selected from the group, wherein the percentage sequence identity is determined by aligning amino acids in the heavy chain variable domains by the Kabat numbering convention.

The invention further provides cell lines producing monoclonal antibodies as described above. Cells lines can be eucaryotic or procaryotic.

The invention further provides methods of determining whether cytocbrome P450 1A2 metabolizes a compound. Such methods entail contacting the compound with cytochrome P450 1A2 in the presence of varying amounts of the binding agent of claim 1. Metabolism of the compound is then assayed as a function of amount of binding agent, a decrease of metabolism with amount of binding agent indicating that cytochrome P450 1A2 metabolizes the compound. In some such methods, the compound is contacted with cytochrome P450 1A2 in a sample containing a collection of cytochrome P450 enzymes including 1A2.

In some methods, the sample is a tissue sample. In some methods, the collection of enzymes are obtained from a cell culture expressing the enzymes. In some methods, the compound is a drug, steroid or carcinogen.

The invention further provides methods of detecting cytochrome p450 1A2. Such methods entail contacting a sample suspected of containing cytochrome P450 1A2 with a binding agent described above. One then determines whether the agent specifically binds to the sample, specific binding indicating the presence of cytochrome P450 1A2 in the sample.

The invention further provides methods of measuring p450 1A2 levels in an individual relative to p450 1A2 levels in a control population. Such methods entail contacting a sample suspected of containing cytochrome P450 1A2 from the individual and a substrate of 1A2. One then determines the p450 1A2 levels in the individual relative to p450 1A2 levels in the control population.

DEFINITIONS

Figure 1:
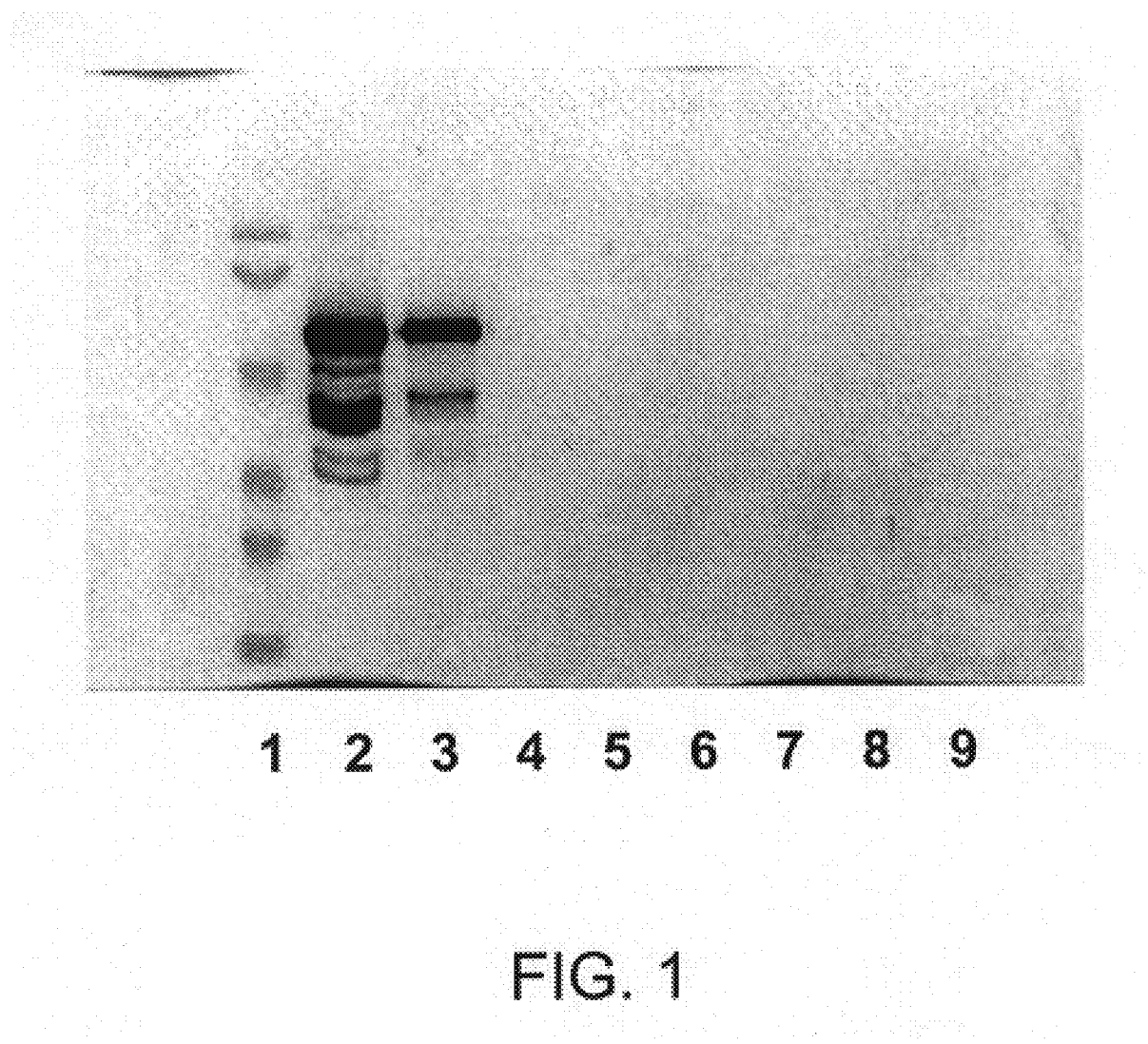
FIG. 1 shows immunoblot analysis of expressed human P450s with MAb 26-7-5. Lane 1 MW standard, 2: baculovirus-expressed 1A2 (0.2 pmol), 3: vaccinia virus-expressed 1A2 (0.2 pmol), 4–8: expressed human 1A1, 2A6, 2C9, 2C19, 2E1, 3A4, respectively (1.5 pmol), Lane 9, wild type vaccinia virus control (30 $\mu$g protein).

Specific binding between an antibody or other binding agent and an antigen means a binding affinity of at least $10^6$ $M^{-1}$. Preferred binding agents bind human cytochrome P450 1A2 with affinities of at least about $10^7$ $M^{-1}$, and preferably $10^8$ $M^{-1}$ to $10^9$ $M^{-1}$ or $10^{10}$ $M^{-1}$.

The term epitope means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The phrase "substantially identical," in the context of two nucleic acids or polypeptides (e.g., DNAs encoding a humanized immunoglobulin or the amino acid sequence of the humanized immunoglobulin) refers to two or more sequences or subsequences that have at least about 80%, most preferably 90–95% or higher nucleotide or amino acid residue identity, when compared and aligned for maximum correspondence, as measured using the following sequence comparison method and/or by visual inspection. Such "substantially identical" sequences are typically considered to be homologous. Preferably, the "substantial identity" exists over a region of the sequences that is at least about 50 residues in length, more preferably over a region of at least about 100 residues, and most preferably the sequences are substantially identical over at least about 150 residues, or over the full length of the two sequences to be compared. As described below, any two antibody sequences can only be aligned in one way, by using the numbering scheme in Kabat. Therefore, for antibodies, percent identity has a unique and well-defined meaning. That is, percent sequence identity is the percentage of aligned amino acids or nucleotides that are the same between two immunoglobulins or their coding sequences being compared.

Amino acids from the variable regions of the mature heavy and light chains of immunoglobulins are designated Hx and Lx respectively, where x is a number designating the position of an amino acids according to the scheme of Kabat et al., *Sequences of Proteins of Immunological Interest* (National Institutes of Health, Bethesda, Md. (1987) and (1991)) Kabat et al. list many amino acid sequences for antibodies for each subclass, and list the most commonly occurring amino acid for each residue position in that subclass. Kabat et al. use a method for assigning a residue number to each amino acid in a listed sequence, and this method for assigning residue numbers has become standard in the field. Kabat et al's scheme is extendible to other antibodies not included in the compendium by aligning the antibody in question with one of the consensus sequences in Kabat et al. The use of the Kabat et al. numbering system readily identifies amino acids at equivalent positions in different antibodies. For example, an amino acid at the L50 position of a human antibody occupies the equivalence position to an amino acid position L50 of a mouse antibody.

The term antibody is used to mean whole antibodies and binding fragments thereof.

An isolated species means an object species (e.g., a binding polypeptide of the invention) that is the predominant species present (i. e., on a molar basis it is more abundant than any other individual species in the composition). Preferably, an isolated species comprises at least about 50, 80 or 90 percent (on a molar basis) of all macromolecular species present. Most preferably, the object species is purified to essential homogeneity (contaminant species cannot be detected in the composition by conventional detection methods).

DESCRIPTION OF THE SPECIFIC EMBODIMENTS

The invention provides monoclonal antibodies and other binding agents in isolated form that specifically bind to human cytochrome P450 1A2, and inhibit enzymic activity of 1A2. Preferred agents lack specific binding to other human cytochromes P450. The invention further provides methods of using the antibodies and other binding agents in identifying individuals with a deficient metabolizing 1A2 phenotype, and in screening drugs for metabolism by cytochrome P450 1A2.

I. Binding Agents of the Invention
A. Specificity and Functional Properties

Binding agents of the invention compete with exemplary antibodies designated MAb 26-7-5 (ATCC HB-12681), MAB 951-5-1 (ATCC HB-12684) and MAb 1812-4-8 (ATCC HB-12683) for specific binding to human cytochrome P450 1A2. Production of monoclonal antibodies MAb 26-7-5, MAB 951-5-1 and MAb 1812-4-8 is described in the Examples. The data in the Examples show that out of the total repertoire of antibodies to human cytochrome P450 1A2, only a small proportion inhibit 1A2 enzymic activity. Binding agents that compete with MAb 26-7-5, MAB 951-5-1 or MAb 1812-4-8 for binding to cytochrome P450 1A2 are expected to share similar inhibitory properties because inhibition by the exemplified antibodies likely arises through binding of the exemplified antibodies to an active site of 1A2, and competing agents bind to the same or closely proximate site as MAb 26-7-5, MAB 951-5-1 or MAb 1812-4-8. Capacity to compete with MAb 26-7-5, MAB 951-5-1 or MAb 1812-4-8, thus defines a select subclass of antibodies with advantageous properties from the total repertoire of antibodies to human cytochrome P450 1A2 MAb 26-7-5, MAB 951-5-1 and MAb 1812-4-8 are further characterized by binding to human 1A2 on an immunoblot indicating these antibodies bind to epitope(s) that are not lost on treatment with a denaturing solvent.

Hybridomas producing MAb 26-7-5 (ATCC HB-12681), MAb 951-5-1 (ATCC HB-12684) and MAb 1812-4-8 (ATCC HB-12683) have been deposited with the American Type Culture Collection, 10801 University Boulevard, Manassas, Va. 20110-2209 under the Budapest Treaty and given the Accession Nos. indicated on Mar. 18, 1999. These cell lines will be maintained at an authorized depository and replaced in the event of mutation, nonviability or destruction for a period of at least five years after the most recent request for release of a sample was received by the depository, for a period of at least thirty years after the date of the deposit, or during the enforceable life of the related patent, whichever period is longest. All restrictions on the availability to the public of these cell lines will be irrevocably removed upon the issuance of a patent from the application.

Competition is determined by an assay in which the antibody under test inhibits specific binding of a reference antibody to an antigenic determinant on human cytochrome P450 1A2. Numerous types of competitive binding assays are known for example: (See Harlow and Lane, "*Antibodies, A Laboratory Manual,*" Cold Spring Harbor Press (1988)). Typically, such an assay involves the use of purified human cytochrome P450 1A2, an unlabelled test antibody and a labeled reference antibody. ompetitive inhibition is measured by determining the amount of label bound to human ytochrome P450 1A2 in the presence of the test antibody. Usually the test antibody is present in excess. Antibodies identified by competition assay (competing antibodies) include antibodies binding to the same epitope as a reference antibody and antibodies binding to an adjacent epitope sufficiently proximal to the epitope bound by the reference antibody for steric hindrance to occur. Usually, when a competing antibody is present in excess, it will inhibit specific binding of a reference antibody to human cytochrome P450 1A2 by at least 10, 25, 50 or 75%.

Binding agents of the invention typically lack specific binding (i. e., crossreactivity) to human cytochromes P450 other than 1A2, so that the binding agents can be used to detect human cytochrome P450 1A2 in the presence of other cytochromes P450. For example, binding agents of the invention typically lack specific binding to one or more of human cytochromes P450 1A1, 2A6, 2B6, 2C8, 2C9, 2C18, 2C19, 2D6, 2E1, 3A4, and 3A5 as measured by ELISA and immunoblot. Some binding agents of the invention, including the exemplified MAb 26-7-5, MAb 95 1-5-1, and MAb 1812-4-8 lack specific binding to all of the above human cytochromes P450.

As noted above, binding agents of the invention are characterized by capacity to inhibit human cytochrome P450 1A2-catalyzed metabolism of a substrate known to be metabolized by the enzyme. The enzyme can be assayed with any of phenacetin, 7-ethoxycoumarin, chlorzoazone or phenanthrene as the substrate (See present Examples). Assays can be performed in either a microsome systems or a reconstituted systems of purified enzymes. For example, a suitable microsome system contains 1 mg/ml protein of human liver microsomes or 1.6 mg protein/ml from human lymphoblast cell lines, together with 0.2 mM substrate in a final volume of 1.0 ml of 100 mM potassium phosphate buffer, pH 7.5, and 1 mM NADPH. An exemplary reconstituted system, in place of the microsome system, contains about 20–50 nM purified human P450 1A2, 40–100 nM cytochrome b5, 100 nM NADPH-P450 reductase, 10 µg/ml phospholipids and 0.25 mM sodium cholate. Incubations are typically carried out at 37° C. for 30 min. Percentage inhibition is defined as 1- (rate of formation metabolic product in presence of test antibody/rate of formation of metabolic product in presence of control antibody), when antibody is present in excess. (The control antibody is an antibody lacking specific binding to human cytochrome P450 1A2.) Some agents of the invention inhibit metabolic capacity of isolated pure cytochrome P450 1A2 on any or all of the above substrates by at least 25%, 50%, 75%, 85%, 90% or 95%.

B. Antibodies of the Invention

1. General Characteristics

The basic antibody structural unit is known to comprise a tetramer. Each tetramer is composed of two identical pairs of polypeptide chains, each pair having one "light" (about 25 kDa) and one "heavy" chain (about 50–70 kDa). The amino-terminal portion of each chain includes a variable region of about 100 to 110 or more amino acids primarily responsible for antigen recognition. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (See generally, *Fundamental Immunology*(Paul, W., ed., 2nd ed. Raven Press, N.Y., 1989), Ch. 7 (incorporated by reference in its entirety for all purposes).

The variable regions of each light/heavy chain pair form the antibody binding site. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. CDR and FR residues are delineated according to the standard sequence definition of Kabat et al, supra. An alternative structural definition has been proposed by Chothia et al., *J. Mol. Biol.* 196, 901–917 (1987); Nature 342, 878–883 (1989); and *J Mol. Biol.* 186, 651–663 (1989).

2. Production

Antibodies to human cytochrome P450 1A2 can be produced by a variety of means. The production of non-human monoclonal antibodies, e.g., munine or rat, can be accomplished by, for example, immunizing the animal with a preparation containing purified human cytochrome P450 or a fragment thereof. The immunogen can be obtained from a natural source, by peptides synthesis or preferably by recombinant expression. Antibody-producing cells obtained from the immunized animals are immortalized and screened for the production of an antibody which binds to human cytochrome P450 or a fragment thereof. See Harlow & Lane, *Antibodies, A Laboratory Manual* (CSHP NY, 1988) (incorporated by reference for all purposes).

Humanized forms of mouse antibodies can be generated by linking the CDR regions of non-human antibodies to human constant regions by recombinant DNA techniques. See Queen et al., *Proc. Natl. Acad. Sci.* USA 86, 10029–10033 (1989) and WO 90/07861 (incorporated by reference for all purposes).

Human antibodies can be obtained using phage-display methods. See, e.g., Dower et al., WO 91/17271; McCafferty et aL, WO 92/01047. In these methods, libraries of phage are produced in which members display different antibodies on their outersurfaces. Antibodies are usually displayed as $F_v$ or Fab fragments. Phage displaying antibodies with a desired specificity are selected by affinity enrichment to human cytochrome P450 or a fragment thereof. Human antibodies are selected by competitive binding experiments, or otherwise, to have the same epitope specificity as a particular mouse antibody, such as MAb 26-7-5, MAb 95 1-5-1, and MAb 1812-4-8. Such antibodies are particularly likely to share the useful functional properties of the exemplified antibodies.

3. Antibody Fragments

Antibodies of the invention include intact antibodies and fragments. Typically, these fragments compete with the intact antibody from which they were derived for specific binding to human cytochrome P450 1A2, and bind with an affinity of at least $10^6$, $10^7$, $10^8$, $10^9$ $M^{-1}$, or $10^{10}$ $M^{-1}$. Antibody fragments include separate heavy chains, light chains Fab, Fab' F(ab')$_2$, Fv, and single chain antibodies comprises a heavy chain variable region linked to a light chain variable region via a peptide spacer. Fragments can be produced by enzymic or chemical separation of intact immunoglobulins. For example, a F(ab')$_2$ fragment can be obtained from an IgG molecule by proteolytic digestion with pepsin at pH 3.0–3.5 using standard methods such as those described in Harlow and Lane, supra. Fab fragments may be obtained from F(ab')$_2$ fragments by limited reduction, or from whole antibody by digestion with papain in the presence of reducing agents. (See id.) Fragments can also be produced by recombinant DNA techniques. Segments of nucleic acids encoding selected fragments are produced by digestion of full-length coding sequences with restriction enzymes, or by de novo synthesis. Often fragments are expressed in the form of phage-coat fusion proteins. This manner of expression is advantageous for affinity-sharpening of antibodies.

4. Recombinant Expression of Antibodies

Nucleic acids encoding light and heavy chain variable regions, optionally linked to constant regions, are inserted into expression vectors. The light and heavy chains can be cloned in the same or different expression vectors. The DNA segments encoding antibody chains are operably linked to control sequences in the expression vector(s) that ensure the expression of antibody chains. Such control sequences include a signal sequence, a promoter, an enhancer, and a transcription termination sequence. Expression vectors are typically replicable in the host organisms either as episomes or as an integral part of the host chromosome.

E. coli is one procaryotic host particularly for expressing antibodies of the present invention. Other microbial hosts suitable for use include bacilli, such as Bacillus subtilus, and other enterobacteriaceae, such as Salmonella, Serratia, and various Pseudomonas species. In these prokaryotic hosts, one can also make expression vectors, which typically contain expression control sequences compatible with the host cell (e.g., an origin of replication) and regulatory sequences such as a lactose promoter system, a tryptophan (trp) promoter system, a beta-lactamase promoter system, or a promoter system from phage lambda.

Other microbes, such as yeast, may also be used for expression. Saccharomyces is a preferred host, with suitable vectors having expression control sequences, such as promoters, including 3-phosphoglycerate kinase or other glycolytic enzymes, and an origin of replication, termination sequences and the like as desired.

Mammalian tissue cell culture can also be used to express and produce the antibodies of the present invention (See Winnacker, *From Genes to Clones* (VCH Publishers, N.Y., 1987). Eukaryotic cells are preferred, because a number of suitable host cell lines capable of secreting intact antibodies have been developed. Preferred suitable host cells for expressing nucleic acids encoding the immunoglobulins of the invention include: monkey kidney CV1 line transformed by SV40 (COS-7, ATCC CRL 1651); human embryonic kidney line (293) (Graham et al., *J. Gen. Virol.* 36:59 (1977)); baby hamster kidney cells (BHK, ATCC CCL 10); Chinese hamster ovary-cells-DHFR (CHO, Urlaub and Chasin, *Proc. Natl. Acad. Sci.* (USA) 77:4216 (1980)); mouse sertoli cells (TM4, Mather, *Biol. Reprod.* 23:243–251 (1980)); monkey kidney cells (CV1 ATCC CCL 70); african green monkey kidney cells (VERO-76, ATCC CRL 1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); and, TRI cells (Mather et al., *Annals N.Y. Acad. Sci.* 383:44–46 (1982)); baculovirus cells.

The vectors containing the polynucleotide sequences of interest (e.g., the heavy and light chain encoding sequences and expression control sequences) can be transferred into the host cell. Calcium chloride transfection is commonly utilized for prokaryotic cells, whereas calcium phosphate treatment or electroporation can be used for other cellular hosts. (See generally Sambrook et al., *Molecular Cloning: A Laboratory Manual* (Cold Spring Harbor Press, 2nd ed., 1989) (incorporated by reference in its entirety for all purposes). When heavy and light chains are cloned on separate expression vectors, the vectors are co-transfected to obtain expression and assembly of intact immunoglobulins. After introduction of recombinant DNA, cell lines expressing immunoglobulin products are cell selected. Cell lines capable of stable expression are preferred (i. e., undiminished levels of expression after fifty passages of the cell line).

Once expressed, the whole antibodies, their dimers, individual light and heavy chains, or other immunoglobulin forms of the present invention can be purified according to standard procedures of the art, including ammonium sulfate precipitation, affinity columns, column chromatography, gel electrophoresis and the like (*See generally ScoPes, Protein Purification* (Springer-Verlag, N.Y., 1982). Substantially pure immunoglobulins of at least about 90 to 95% homogeneity are preferred, and 98 to 99% or more homogeneity most preferred.

5. Screening for Sequence Analogs

Many of the antibodies described above can undergo non-critical amino-acid substitutions, additions or deletions in both the variable and constant regions without loss of binding specificity or effector functions, or intolerable reduction of binding affinity (i. e., below about $10^6$ $M^{-1}$) for human cytochrome P450 1A2. Usually, the light and heavy chain variable regions of immunoglobulins incorporating such alterations exhibit at least 80, 90 or 95% sequence identity to the corresponding regions of a reference immunoglobulin from which they were derived, such as MAb 26-7-5, MAb 951-5-1 and MAb 1812-4-8. Preferred antibody light and heavy chain sequence variants have the same complementarity determining regions (CDRS) as the corresponding chains from one of the above reference antibodies. Occasionally, a mutated immunoglobulin can be selected having the same specificity and increased affinity compared with a reference immunoglobulin from which it was derived. Phage-display technology offers powerful techniques for selecting such immunoglobulins. See, e.g., Dower et al., WO 91/17271 McCafferty et al., WO 92/01047; Huse, WO 92/06204.

C. Other Binding Agents of the Invention

The invention further provides nonantibody binding agents that compete with one of the exemplified antibodies for binding to human cytochrome P450 1A2. These binding agents include polypeptides, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of the compounds can be constructed by the encoded synthetic libraries (ESL) method described in Affymax, WO 95/12608, Affymax, WO 93/06121, Columbia University, WO 94/08051, Pharnacopeia, WO 95/35503 and Scripps, WO 95/30642 (each of which is incorporated by reference for all purposes). Peptide libraries can also be generated by phage display methods. See, e.g., Devlin, WO 91/18980. The libraries of compounds are screened for binding to human cytochrome P450 in competition with one of the reference antibodies MAb 26-7-5, MAB 951-5-1 or MAb 1812-4-8.

II. Human Cytochrome P450 1A2

The cDNA for human cytochrome P450 1A2 has been cloned, sequenced, and expressed (See e.g., Battula et aL, 1987; Yang et al., 1998). Sources of other cytochromes P450 (e.g., for use in testing for lack of crossreactivity) are described by Nebert, *DNA & Cell Biol.* 10, 1–14 (1991); Nelson et al., *Pharmacogenetics* 6, 1–42 (1996). Insect cells (e.g., SF9) with appropriate vectors, usually derived from baculovirus, are also suitable for expressing 1A2 and other cytochromes P450. See Luckow et al., *Bio/Technology* 6:47–55 (1988); Gonzalez et al., *Meth. Enzymol.*, 206, 93–99 (1991) (incorporated by reference for all purposes). Other expression systems include yeast (Ellis et aL., supra), E. coli (Gillamn et al., *Archives Biochem. Biophys.* 319, 540–550 (1995); vaccinia virus (Gonzalez, *Pharmacol. Res.* 40, 243 (1989), and human AHH-1 lymphoblastoid cells (Crespi et al., *Carcinogenesis* 10, 295–301(1989)).

Humans shows a wide range of the activities. Variations of P450 activity in a tissue can result from a variety of factors including nutritional factors, chemical inducers in the environent, age, sex and general physiological or disease condition of the subject individual. MAbs to 2A6 can define the P450 variations related to genetic, age, sex, nutritional and environmental influences on P450 metabolism. The role in the metabolism of a drug by a single or multiple P450s can be important in drug discovery for understanding P450 dependent partner drug relationships that can be toxic. The P450s can be major control elements of the metabolic rates of drug metabolism as well as their pharmacologic character. The MAbs can also identify drugs toxic due to the absence of a polymorphic P450. This information can lead to better understanding of P450 activity in drug choice, dosage and efficacy.

Several therapeutically important compounds are metabolized by 1A2. The list includes phenacetin, R-w arfarin, clomiprachine, imipramine, theophyline, theobromine, paraxanthine, caffeine, chlorzoxazone, 7-methoxyresorufin, and 7-ethoxycoumarin. P450 1A2 is also has a major role in activating mutagens and carcinogens. For example, 1A2 metabolically activates the food pyrolysis products IQ and MeIQx to active mutagens (Edwards et al., 1994; Rendic et al., 1997).

III. Methods of Use

A. Identifying Compounds Metabolized by 1A2

Binding agents of the invention that inhibit enzymic activity of human cytochrome P450 1A2 can be used to assay whether compounds are metabolized by 1A2. Compounds include xenobiotics, such as a currently used and new drugs, carcinogens, pesticides or other industrial or environmental chemicals, or any endobiotic, such as a steroid hormone. The assay canindicate not only that a compound is metabolized by 1A2 but also the contribution of 1A2 to metabolizing the compound relative to other cytochromes P450 present in microsomes or cell homogenates.

Assays are performed by contacting a compound under test with human cytochrome P450 1A2 in reaction mixtures containing varying amounts of a binding agent of the invention. For example, two separate reactions may be set up, one in which the binding agent of the invention is present, and the other, a control in which the binding agent is absent. The human cytochrome P450 is often present as a microsomal extract from human or animal cells or cell lines or an extract from cell cultures expressing a collection of recombinant P450s including 1A2. The assay is performed under conditions in which 1A2 is known to be active on known substrates, such as bufurolol (See Examples). Metabolism of the compound under test is then followed from the disappearance of the compound or appearance of a metabolic product of the compound as a function of time (e.g., nmol product/sec). See, e.g., Buters et al., *Drug Metab. Dispos.* 22, 688 (1994). The metabolism of the compound is analyzed as a function of the amount of binding agent present. If the metabolism quantitatively decreases with amount of binding agent, it can be concluded that 1A2 metabolizes the compound.

The percentage inhibition of 1A2 metabolism of a test compound may reflect both the inherent efficiency of a binding agent in blocking 1A2 activity and the contribution of cytochromes P450 other than 1A2 in metabolizing the compound. The inherent blocking efficiency of a binding agent can be determined by measuring inhibition of metabolism in a reaction mixture in which only 1A2 is present, or alternatively, in a reaction mixture in which a collection of cytochromes P450 are present but the substrate is known to be metabolized only by 1A2. Comparison of the percentage inhibition determined in these circumstances with the percentage inhibition of metabolism of a test substrate when a mixture of cytochromes P450 are present indicates the relative contributions of 1A2 and other enzymes in the mixture to metabolism of the test substrate. For example, if metabolism of a control substrate by pure 1A2 is inhibited by a binding agent by 90% and metabolism of a test substrate by a mixture of cytochromes P450 including 1A2 is inhibited 45%, it can be concluded that in the mixture, 1A2 contributes about 45/90=50% of metabolizing activity on the test substrate. Binding agents having a high degree of inhibition (e.g., at least about 90%) of a known substrate are particularly effective for quantitative analysis as described above.

The anti 1A2 Mab can also be used to identify substrates metabolized by CYP1A2 in human liver tissues. Recognition of the nature and contribution of CYP1A2 in individuals can permit studies of drug-drug interactions based on competitive metabolism. MAbs 26-7-5, MAB 951-5-1 and 1812-4-8 can also be used as reagents for CYP1A2 based metabolism studies of procarcinogens and promutagens. These MAbs can also be used in drug metabolism studies for understanding drug disposition, activation and therapeutic applications.

Information made available by the above methods can be exploited in a number of applications. Drugs determined to be processed by 1A2 should in general not be prescribed to patients deficient in 1A2 metabolism, or should be prescribed in reduced amounts or with close monitoring. Particular caution is needed in combination therapies involving two drugs metabolized by the 1A2 pathways. The information can also be valuable in drug design and screening. That is drugs can be designed or screened such that they are metabolized to a significant extent by several P450 enzymes, and are not therefore likely to cause side effects in those deficient in any single enzymes. Recognition that a carcinogen or other environmental toxin is deactivated by 1A2 signals that deficient metabolizers are at particular risk from the carcinogen or compound. Conversely, recognition that a carcinogen or other environmental toxin is activated to harmful form by 1A2 indicates that deficient metabolizers are less prone to harm from exposure to such a compound relative to extensive metabolizers.

B. Use of Agents for Diagnosing P450 Metabolic Variations

The binding agents are useful diagnostics to determine a patient's metabolic profile prior to treatment with a drug known or suspected to be metabolized by 1A2. Patients identified as defective in 1A2 metabolism can be given alternative therapy, a lower dosage or additional monitoring to avoid damaging side effects from their DM phenotype. Diagnosis can be performed as described below.

1. Binding Assay

Binding agents of the invention are useful for the quantitative measurement of the amount of individual P450 proteins in a sample, which may contain multiple forms of other P450 proteins. Binding between binding agent and cytochrome P450 1A2 in the sample can be detected by radioimmunoassay, ELISA or immuno blotting (See Harlow and Lane, supra). The type of immunoassay can be tailored to the particular application. In radioimmunoassay, the binding agent of the invention is typically labeled. In ELISA, the binding agent is typically unlabelled and detected using a secondary labeled reagent with affinity for the binding agent (e.g., anti-IgG$^{35}$S-or $^3$H-labeled MAb). Immuno blots are particularly useful for screening a sample with a panel of antibodies to different cytochromes P450.

These assays can be tailored to measure p450 1A2 levels in an individual relative to p450 1A2 levels in a control population. The method entails contacting a sample suspected of containing cytochrome P450 1A2 from the individual with a 1A2 substrate. One then determines the p450 1A2 levels in the individual relative to the 1A2 levels in a control population.

C. Other Uses

The binding agents of the invention can also be used for affinity purification of cytochrome P450 1A2. The basic procedure for affinity purification requires only one or two steps and can yield highly purified milligram quantities of cytochrome P450 1A2. For example, the binding agent can be covalently bound to Sepharose™, which is made into the form of either column or a slurry for batch purification. A sample containing cytochrome P450 1A2 is them passed through the column or slurry and binds to the binding agent-linked Sepharose™. The nonbound material containing unrelated proteins and cytochromes P450 other than 1A2 are thoroughly eluted leaving the cytochrome P450 1A2, which can then be eluted and used for a variety of chemical and physical studies. See, e.g., Cheng et al., *J Biol. Chem.* 259, 12279–12284 (1948).

Monoclonal antibody based immunohistochemical methods can be applied to localize and examine the distribution cytochrome P450 1A2 after different inducer administration, during various physiological states related to nutrition, age, and sex, and in different species and tissues. Furthermore, the intracellular distribution of the cytochrome P450 1A2 can be determined in a way not possible by standard biochemical methods which generally cannot identify the presence of specific forms of cytochrome P450 proteins in isolated tissues and organelles. See, e.g., Gelboin, *Pharmacol. Rev.* 45, 413–453 (1993).

Variations of P450 activity in a tissue can result from a variety of factors including nutritional factors, chemical inducers in the environment, age, sex and general physiological or disease condition of the subject individual. MAbs to 1A2 can define the P450 variations related to genetic, age, sex, nutritional and environmental influences on P450 metabolism. The role in the metabolism of a drug by a single or multiple P450s can be important in drug discovery for understanding P450 dependent partner drug relationships that can be toxic. The P450s can be major control elements of the metabolic rates of drug metabolism as well as their pharmacologic character. The MAbs can also identify drugs toxic due to the absence of a polymorphic P450. This information can lead to better understanding of P450 activity in drug choice, dosage and efficacy.

EXAMPLES

Materials and Methods

Chemicals

Phenacetin, acetaminophen, acetalinide, 7-ethoxycoumarin, 7-hydroxycoumarin, chlorzoxazone chlorpropamide and NADPH were purchased from Sigma Chemical Co. (St. Louis, Mo.). Phenanthrene (PA) and B[a]P cis 4,5-dihydrodiol were from the NCI Chemical Carcinogen Repository (Kansas City, Mo.). All reagents were of analytical grade.

Preparation of monoclonal antibodies

The previously cloned human P450 1A2 cDNA (Jaiswal et al., 1987) was inserted into a baculovirus vector and Hi-five or Spondoptera Frugipedra (Sf9) cells were infected with the recombinant baculovirus to produce 1A2 (Buters et al., 1994; Gonzalez et al., 1991b). Six female BALB/c mice were immunized by i.p. injection weekly for 3 weeks with 30 mg of 1A2 protein emulsified in 0.2 mL of complete Freund's adjuvant for the first injection, and then with incomplete Freund's adjuvant for subsequent injections. Three days after the third injection, the mouse serum was examined by ELISA. The mice were sacrificed and spleens removed. The hybridoma production, screening by ELISA and IB of MAbs, and MAb content determination are the same as previously described (Gelboin et al., 1996; Gelboin et al., 1995).

Human liver microsomes and cDNA-expressed P450s

Human liver specimens, stored at -80° C. until use, were obtained from organ donors after clinical death (The NCI Cooperative Human Tissue Network, NIH, Bethesda, Md.). Microsomes were prepared as described (Alvares et al., 1970) and microsomal protein (Lowry et aL., 1951) and P450 content (Omura and Sato, 1964) were measured according to published methods.

Recombinant human P450 1A2, 2B6, 2C8, 2C9, 2E1, 3A4 and 3A5 were expressed in Hepa G2 cells using vaccinia virus (Battula et al., 1987; Yang et al., 1998). Microsomes with baculovirus expressed human P450 1A1, 1A2, 2A6, 2C18, 2C19 with NADPH-P450 oxidoreductase co-expressed were obtained from Gentest Corporation (Woburn, Mass.).

MAbs inhibition of 1A2 activity

Inhibition of P450 catalyzed activity was always performed with saturating levels of MAbs yielding maximum inhibition. A typical assay contained MAbs in 5 to 25 µL of ascites with a content at about 400 pmol MAb (IgG). This ascites fluid was preincubated with 25 pmol of 1A2 or 250 pmol of human liver microsomal P450s in 0.5 niL of 50 mM potassium phosphate buffer (KPi, pH 7.4) at 37° C. for 5 min. The mixture was diluted with the buffer to a final volume of 1 mL. The substrate, i. e., phenacetin, chlorzoxazone, 7-ethoxycoumarin or phenanthrene, was dissolved in 10 mL of methanol and added (final concentration at 200 µM), and the reaction was initiated by the addition of NADPH (1mM) at 37° C. Anti-lysozyme MAb (HyHel, IgG), with an amount equivalent to the test MAbs, was used as a control for nonspecific inhibition. Reactions were incubated for 30 min and terminated with 1 mL of acetone. Acetanilide was used as internal standard for the phenacetin metabolism and B[a]P cis 4,5-diol was used as internal standard for the metabolism of 7-ethoxycoumarin. Samples were extracted twice with 7 mL dichloromethane and were dried under N2 and the residue dissolved in mobile phase and immediately analyzed by reversed phase HPLC. The metabolites formed were identified by comparing their retention times with authentic standards.

High Performance Liquid Chromatoraphy

HPLC was performed using a Hewlett-Packard (HP, Rockville, Md., USA) Model HP1050 liquid chromatography system equipped with an HP model 1050 autosampler, a ternary solvent delivery system, and a multiple-wavelength or dioarray detector, which are controlled by the HPLC 2D or 3D ChemStation software installed on a Compaq Deskpro 5133 personal computer (Compaq Computer Cor., Houston, Tex., USA).

Analysis of phenanthrene metabolism (Shou et al., 1994) and chlorzoxazone metabolism (Ono et al., 1995) were previously described, respectively. Analysis of 7-ethoxycoumarin and its metabolite was modified according to Rosenberg et al. (Rosenberg et al., 1990) with a 20/20 ODS column (4.6×250 mm, Thomason Instrument Co., Springfield, Va.). The mobile phase for separation of 7-ethoxycoumarin and its metabolite were methanol/water (25:75 v/v, containing 0.05% acetic acid) to methanol/water (60:40 v/v, containing 0.05% acetic acid) by a linear gradient in 10 min, and then to methanol/water (80:20 v/v, containing 0.05% acetic acid) for the following 10 min. 7-EC and 7-OH EC were detected at uv 320 nm and internal standard was detected at uv 254 nm. For separation of phenacetin and its metabolite (Mineshita et al., 1986), a 20/20 ODS column (4.6×250 mm, 5 µm) was used with a mobile phase of acetonitrile/water (10:90 v/v, 0.05% acetic acid) for 8 min followed by a linear gradient to acetonitrile/water (40:60 v/v, 0.05% acetic acid) for 10 min. The metabolite and substrate were detected at uv 250 nm.

Results

Preparation of MAbs specific to human P450 1A2

The 1A2 cDNA was inserted into a baculovirus vector to produce 1A2 protein for use as immunogen for production of hybridomas. In a first experiment, 1220 hybridomas were screened for a monoclonal antibody with inhibitory properties to 1A2. None was identified. In a second independent experiment, 878 hybridomas were screened, again without identifying any with inhibitory properties. In a third experiment, using a three-week immunization period, the dispersed spleen cells from the immunized mice were fused with myeloma cells resulting in the formation of over 2050 hybridomas. MAbs from 82 hybridomas showed positive binding to 1A2 by ELISA. Twelve of the 82 hybridomas were stable and the MAbs from these hybridomas strongly bound by ELISA both the baculovirus and vaccinia virus-expressed 1A2. Three of the MAbs; MAb 26-7-5 (IgG1), MAB 951-5-1 (IgG1) and MAb 1812-4-8 (IgG1), were subsequently found to inhibit 1A2 enzyme activity and exhibited a strong specific immunoblot. These three MAbs were examined for their cross reactivity with other human P450s.

Figure 2:
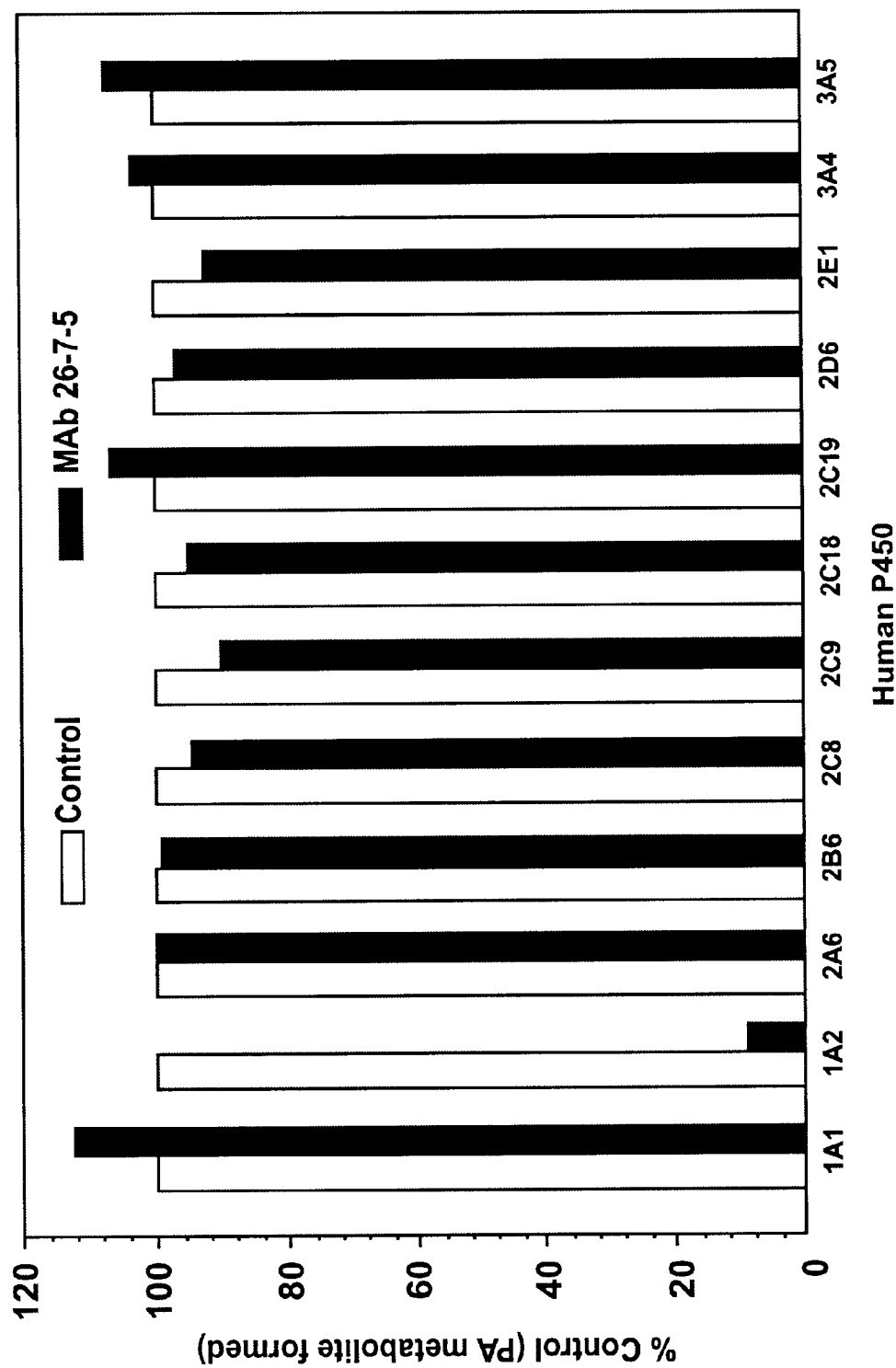
FIG. 2 shows the specificity of MAb 26-7-5 inhibition of phenanthrene metabolism by 12 recombinant human P450s. P450s 1A2, 2B6, 2C8, 2C9, 2E, 3A4 and 3A5 were expressed in Hep G2 cells by recombinant vaccinia virus. 1A1, 2A6 2C18, 2C 19 and 2D6 were expressed in insect cells by baculovirus. The incubation and separation were performed as referenced (Shou et al., 1994). Data is the mean of triplicate determinations. The percent of control is expressed as the ratio of metabolite formed to internal standard in the presence and absence of MAb. Control activities were as follows (nmol/min/nmol P450 of PA 9,10-diol or PA 9-phenol indicated): 1A1(8.8), 1A2 (4.3), 2A6 (3.24, PA 9-phenol), 2B6 (6.58), 2C8 (1.31), 2C9 (4.16), 2C19 (9.84), 2D6 (0.71, PA 9-phenol), 2E1 (1.33), 3A4 (0.72) and 3A5 (0.52).

Table 1 shows the high specificity for 1A2 of the three MAbs. None of the three MAbs cross-reacted with human 1A1, 2A6, 2B6, 2C8, 2C9, 2C18, 2C19, 2D6, 2E1, 3A4, and 3A5 as measured by ELISA and IB. MAb 26-7-5, MAB 951-5-1 and MAb 1812-4-8 exhibit strong immunoblotting to 1A2. FIG. 1 shows the immunoblot analysis of the specificity of MAb 26-7-5, which formed a high specific immunoblot with 1A2. MAb 26-7-5, MAB 951-5-1 and MAb 1812-4-8 inhibited 1A2 catalyzed PA metabolism by about 90% and did not display inhibitory cross reactivity to any of the eleven other human P450s examined (Table 1, FIG. 2). Thus, the immunobinding and inhibitory effect of MAb 26-7-5, MAB 951-5-1 and MAb 1812-4-8 are highly specific to 1A2.

Inhibitory Activity of MAb 26-7-5 Toward 1A2 Enzyme Activity

The metabolism of four substrates of 1A2, phenacetin (von Moltke et al., 1996), 7-ethoxycoumarin (Yamazaki et al., 1996), chlorzoxazone (Ono et al., 1995) and phenanthrene (Shou et al., 1994), were used to measure the inhibitory activity of the MAbs. Table 2 shows that the inhibitory activity of the three MAbs toward the 1A2-catalyzed metabolism ranged from 85–92% with the ratio of P450/MAb being about 1:16 (pmol/pmol). The three MAbs are thus sensitive and precise probes for measuring 1A2-catalyzed metabolism in human liver and other tissues.

Contribution of 1A2 and other P450s to phenacetin metabolism in HLM

Figure 3:
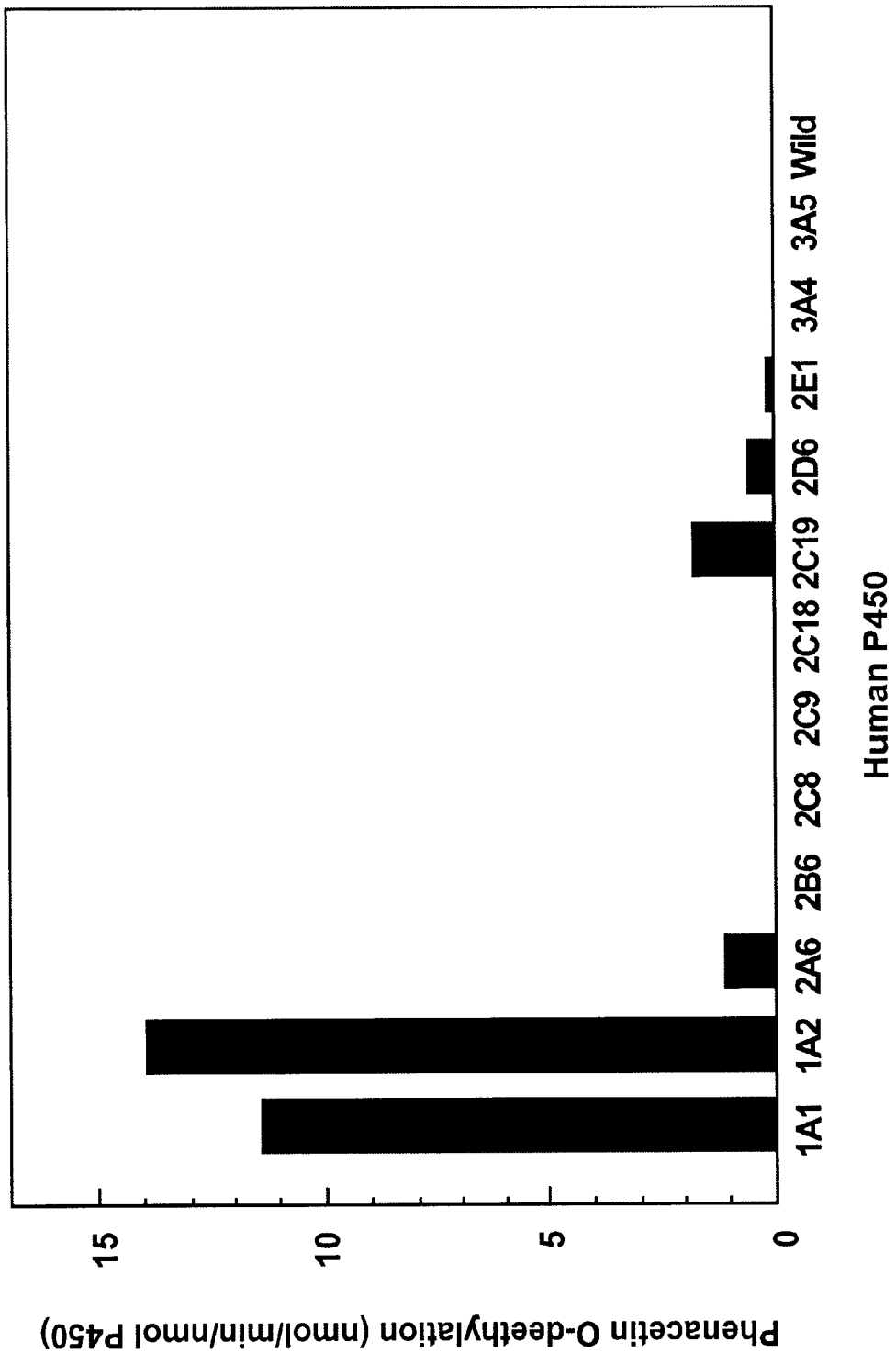
FIG. 3 shows phenacetin O-deethylation by twelve expressed human P450s. P450 1A2, 2B6, 2C8, 2C9, 2E1, 3A4 and 3A5 were expressed in Hep G2 cells by vaccinia virus. P450 1A1, 2A6, 2C18, 2C19 and 2D6 were expressed in insect cells by baculovirus. WT is Hep G2 cells infected with wild vaccinia virus. The incubation and separation were performed as described in Materials and Methods. Data is the mean of three separate determinations.

Phenacetin is mainly metabolized to the commonly used analgesic acetaminophen via O-deethylation catalyzed by P450 1A2 (Rendic et al., 1997; von Moltke et al., 1996). Table 3 shows that the addition of the anti-1A2 MAb 26-7-5 to HLM inhibited the deethylation by 64 to 80% indicating the amount of the metabolism catalyzed by 1A2. Thus the 20–36% of metabolism that is not inhibited must be the result of catalytic activity of P450s other than 1A2. In order to identify the P450s possibly involved in phenacetin O-deethylation, twelve recombinant human P450s were used to determine their catalytic activity for phenacetin O-deethylation (FIG. 3). A high level of O-deethylation activity was exhibited by both 1A1 and 1A2 followed by 2C19 and 2A6. The 2D6 and 2E1 exhibited low activity. No O-deethylation activity was observed with 2B6, 2C8, 2C9, 2C18, 3A4 and 3A5. The result indicates that P450s other than 1A2, i.e., 2C19 and 2A6, participated in phenacetin O-deethylation. Although recombinant 1A1 exhibits high O-deethylation activity, 1A1 content in normal human liver is very low or undetectable (Guengerich, 1995) and thus was not a factor in the HLM experiments.

Specific inhibitory MAbs to the target P450s are simple and useful tools to determine the metabolic contribution of individual P450s in human tissues and liver (Gelboin et al., 1997). We have previously made specific inhibitory MAbs to human P450 1A1, 2B6, 2C8/9/18/19, 2D6, 2E1, and 3A4/5. We have recently made MAb 151-45-4 to human 2A6, which specifically inhibits 2A6 enzyme activity by more than 90% and shows no cross inhibition of other human P450s (unpublished results).

We used the inhibitory antibodies to assess the role of 1A2 and other P450s in the metabolism of phenacetin in human liver samples (Table 3). Eight human liver microsome samples showed a variation in phenacetin O-deethylation activity that ranged from 0.44 to 2.5 nmol/min/nmol P450 (Table 3). Samples of human liver microsomes, exhibiting different levels of phenacetin O-deethylation, were examined for their sensitivity to inhibition by the addition of the inhibitory antibodies to 1A2, 2C19, 2A6, and 1A1, 2D6 and 2E1 (Table 3). The range of the enzyme activity contributed by the different P450s is from 64–84% for 1A2, 4.6–20% for 2C19, 0–9% for 2A6, and 0.5–4.5% for 2D6, 2E1 and 1A1. For example, the O-deethylation of HL74 was inhibited by 64% indicating about a 64% contribution of 1A2 to its total O-deethylation activity. MAb 1-68-11 which is highly inhibitory to 2C8/9/18/19, inhibited O-deethylation activity by 10%, indicating the contribution of 2C19 to phenacetin metabolism in HL74 because expressed P450 2C8/9/18 do not catalyze the metabolism of phenacetin (FIG. 3). P450 2A6 showed activity with about 9% contribution in this liver sample. In HL80, 1A2 contributed 80% of the O-deethylation activity, 2C19 contributed 9.2%, and 2A6 contributed 1%. And the contribution of the different P450s to HL81 was 67% for 1A2, 20% for 2C19, 0.5% for 2A6. The inhibitory MAbs identified and quantitatively assessed the role and variety of the relevant P450s in O-deethylation in HLM from different human samples. The addition of the antibodies to P450 1A2, 2C9 and 2A6 results in an inhibition of O-deethylation activity by 89%, which indicates that the three P450s, 1A2, 2C19, 2A6, are responsible for almost all of the phenacetin O-deethylation activity in human liver.

Figure 4:
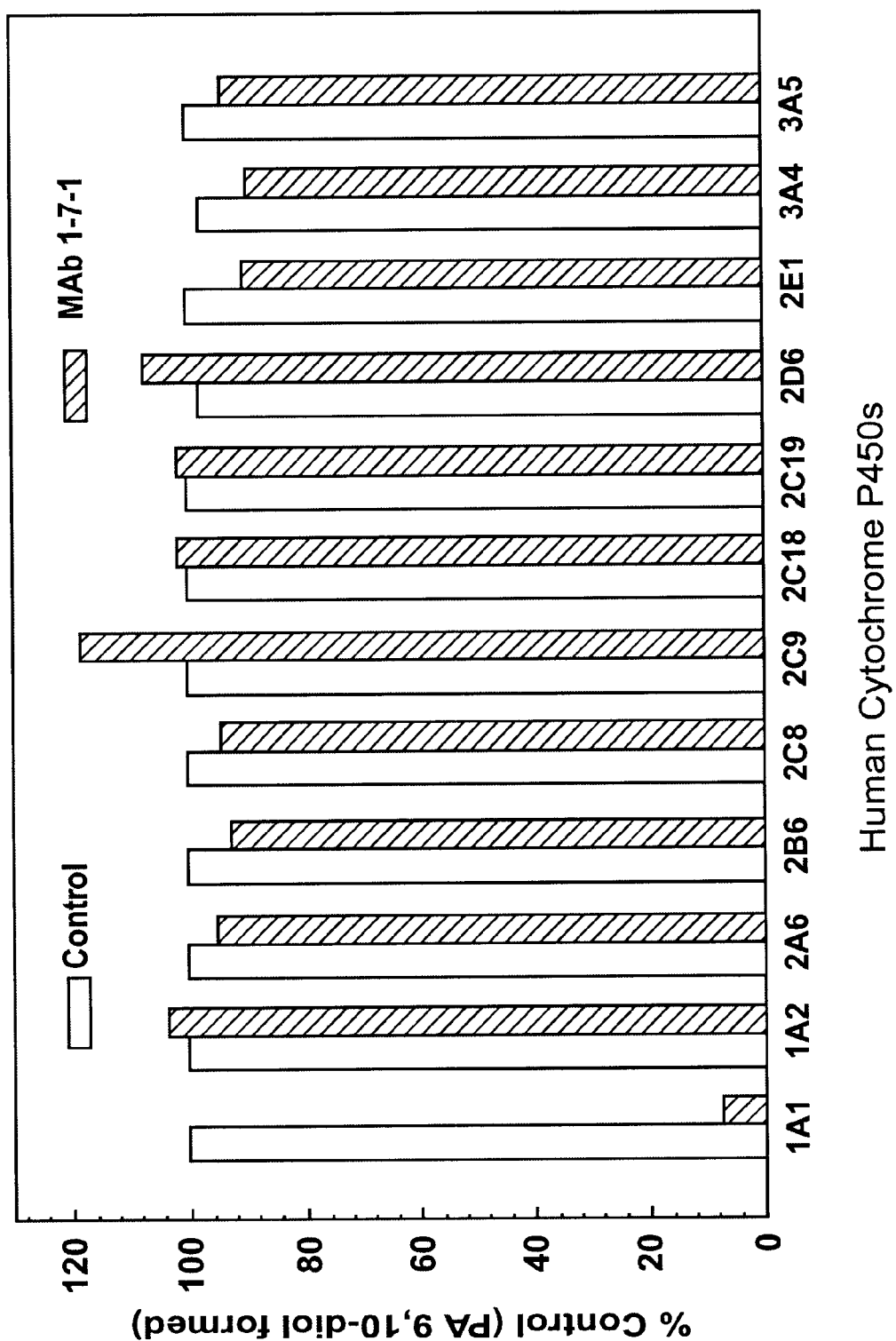
FIG. 4 shows the specificity of MAb 1-7-1 inhibition of phenanthrene metabolism by twelve expressed human P450s. P450 1A2, 2B6, 2C8, 2C9, 2E1, 3A4 and 3A5 were expressed in Hep G2 cells by recombinant vaccinia virus. 1A1, 2A6 2C18, 2C 19 and 2D6 were expressed in insect cell by baculovirus. The incubations and separations were as described previously (Shou et al., 1994). Data is the mean of three incubations.

In addition, we recently found that MAb 1-7-1, which is an MAb to rat 1A1/2 (Park et al., 1982), specifically inhibited human P450 1A1 catalyzed metabolism of phenanthrene and did not crossreact with human P450 1A2 and ten other human P450s (FIG. 4). MAb 1-7-1 inhibited 1A1 catalyzed phenanthrene, 7-ethoxycoumarin, and phenacetin by more than 90%. 1A1 content is expressed little, if at all, in normal human liver (Guengerich, 1995). Thus, MAb 1-7-1 is a useful specific inhibitor for studying 1A1 related P450 metabolism in extrahepatic tissues.

Although the foregoing invention has been described in detail for purposes of clarity of understanding, it will be obvious that certain modifications may be practiced within the scope of the appended claims. All publications and patent documents cited herein are hereby incorporated by reference in their entirety for all purposes to the same extent as if each were so individually denoted.

REFERENCES

1. Alvares, A. V. et al., Studies on the hydroxylation of 3,4-benzpurene by hepatic microsomes. Effect of Albumin on the rate of hydroxylation of 3,4-benzpyrene. *Biochem Pharmacol* 1970: 19, 1449–1455.
2. Battula, N. et al., Expression of P1-450 and P3-450 DNA coding sequences as enzymatically active cytochromes P-450 in mammalian cells. *Proc Natl Acad Sci U S A* 1987: 84, 4073–7.
3. Buters, J. T. M. et at., cDNA-directed expression of human cytochrome P450 CYP3A4 using baculovirus. *Drug Metabolism and Disposition* 1994: 22, 688–692.
4. Edwards, R. J. et al., Contribution of CYP1A1 and CYP1A2 to the activation of heterocyclic amines in monkeys and human. *Carcinogenesis* 1994: 22,688–692.
5. Gelboin, H. V. Cytochrome P450 and monoclonal antibodies. *Pharmacol Rev* 1993: 45, 413–53.
6. Gelboin, H. V. et al., Inhibitory and noninhibitory monoclonal antibodies to human cytochrome P450 2E1. *Chem Res Toxicol* 1996 9, 1023–30.
7. Gelboin, H. V. et al., Inhibitory and non-inhibitory monoclonal antibodies to human cytochrome P450 3A3/4. *Biochem Pharmacol* 1995: 50, 1841–50.

8. Gelboin H. V. et al., Inhibitiory monoclonal antibodies define the role of cytochrome P450 in human tissue: polymorphically expressed P450 2D6 as paradigm. *Pharmacogenetics* 1997: 7, 467–477.
9. Gonzalez, F. J. et al., cDNA-expressed human cytochrome P450s: a new age of molecular toxicology and human risk assessment. *Mutat. Res.* 1991a: 247, 113–127.
10. Gonzalez, F. J. et al., Expression of mammalian cytochrome P450 using baculovirus. *Methods Enzymol* 1991b: 206, 93–99.
11. Guengerich, F. P. Human cytochrome P450 enzymes. In: P. R. Ortiz de Montellano, Ed. Cytochrome P450: structure, mechanism, and biochemistry. *New York: Plenun, Press*, 1995: 473–535.
12. Jaiswal, A. K. et al., Human P(3)450: cDNA and complete protein sequence, repetitive Alu sequences in the 3' nontranslated region, and localization of gene to chromosome 15. *J Exp Pathol* 1987: 3, 1–17.
13. Krausz, K. W. et al., Inhibitory monoclonal antibodies to human cytochrome P450 2D6. *Biochem Pharmacol* 1997: 54, 15–17.
14. Lowry, O. H. et al., Protein measurement with the Folin phenol reagent. *J Biol Chem* 1951: 193, 265–275.
15. Mineshita, S. et al., Determination of phenacetin and its major metabolites in human plasma and urine by high-performance liquid chromatography. *J Chromatogr* 1986: 380, 407–13.
16. Nelson, D. R. et al., P450 superfamily: update on new sequences, gene mapping, accession numbers and nomenclature. *Pharmacogenetics* 1996: 6, 1–42.
17. Omura, T. et al., The carbon monoxide-binding pigment of liver microsomes. I. Evidence for its hemoprotein nature. *J Biol Chem* 1964: 239, 2370–2378.
18. Ono, S. et al., Chlorzoxazone is metabolized by human CYP1A2 as well as by human CYP2E1. *Pharmacogenetics* 1995: 5. 143–50.
19. Park, S. S. et al., Mononclonal antibodies that inhibit enzyme activity of 3-methylcholanthrene-induced cytochrome P-450. *Cancer Res* 1982: 42, 1798–808.
20. Park, S. S. et al., Monoclonal antibodies to rat liver cytochrome P-450 2c/RLM5 that regiospecifically inhibit steroid metabolism. *Biochem Pharmacol* 1989: 38, 3067–74.
21. Rendic, S. et al., Human cytochrome P450 enzymes: a status report summarizing their reactions, substrates, inducers, and inhibitors. *Drug Metab Rev* 1997: 29, 413–580.
22. Rosenberg, D. W. et al., A fluorometric method for measuring ethoxycoumarin O-demethylase activity by reversed-phase high performance liquid chromatography. *Analytical Biochemistry* 1990: 191, 354–358.
23. Shou, M. et al., Regio- and stereo-selective metabolism of phenanthrene by twelve cDNA-expressed human, rodent, and rabbit cytochromes P-450. *Cancer Lett* 1994: 83, 305–13.
24. Tassaneeyakul, W. et al., Specificity of substrate and inhibitor probes for human cytochromes P450 1A1 and 1A2. *J Pharmacol Exp Ther* 1993: 265, 401–7.
25. Vermeulen, N. P. E. Role of metablism in chemical toxicity. In: C. Ioannides, Ed. Cytochromes P450: metabolic and toxicological aspects. *New York: CRC Press*, 1996: 29–53.
26. von Moltke, L. L. et al., Phenacetin O-deethylation by human liver microsomes in vitro: inhibition by chemical probes, SSRI antidepressants, nefazodone and venlafaxine. *Psychopharmacology* (Berl) 1996: 128, 398–407.
27. Yamazaki, H. et al., 7-Ethoxycoumarin O-deethylation catalyzed by cytochromes P450 1A2 and 2E1 in human liver microsomes. *Biochem Pharmacol* 1996: 51, 313–9.
28. Yang, T. J. et al., An inhibitory monoclonal antibody to human cytochrome P450 2B6. *Biochem. Phamacol.* 1998: 55(10), 1633–40.
29. Yang, T. J. et al., Role of cDNA-expressed human cytochromes P450 in the metabolism of diazepam. *Biochemical Pharmacology* 1998: 55(6), 889–96.

What is claimed is:

1. A monoclonal antibody selected from the group consisting of MAb 26-7-5 (ATCC HB-12681), MAB 951-5-1 (ATCC HB-12684), and MAb 1812-4-8 (ATCC HB-12683) for specific binding to human cytochrome P450 1A2, and that specifically inhibits 1A2-catalyzed metabolism of phenacetin by at least 50%.

2. The monoclonal antibody of claim 1 that lacks specific binding to at least one cytochrome P450 selected from the group consisting of human cytochromes P450 1A1, 2A6, 2B6, 2C8, 2C9, 2C18, 2C19, 2D6, 2E1, 3A4, and 3A5.

3. The monoclonal antibody of claim 1 that lacks specific binding to each of human cytochromes P450 1A1, 2A6, 2B6, 2C8, 2C9, 2C18, 2C19, 2D6, 2E1, 3A4, and 3A5.

4. The monoclonal antibody of claim 1 that specifically inhibits the enzyme activity of human cytochrome P450 1A2 by at least 80%.

5. The monoclonal antibody of claim 1 that is MAb 26-7-5 (ATCC HB-12681) or a binding fragment thereof.

6. The monoclonal antibody of claim 1 that is MAb 951-5-1 (ATCC HB-12684) or a binding fragment thereof.

7. The monoclonal antibody of claim 1 that is MAb 1812-4-8 (ATCC HB-12683) or a binding fragment thereof.

8. The monoclonal antibody of claim 1 that is a mouse antibody.

* * * * *